US007250289B2

(12) United States Patent
Zhou

(10) Patent No.: US 7,250,289 B2
(45) Date of Patent: Jul. 31, 2007

(54) METHODS OF GENETIC ANALYSIS OF MOUSE

(75) Inventor: Xue Mei Zhou, San Jose, CA (US)

(73) Assignee: Affymetrix, Inc., Santa Clara, CA (US)

(*) Notice: Subject to any disclaimer, the term of this patent is extended or adjusted under 35 U.S.C. 154(b) by 275 days.

(21) Appl. No.: 10/719,900

(22) Filed: Nov. 20, 2003

(65) Prior Publication Data

US 2005/0026164 A1 Feb. 3, 2005

Related U.S. Application Data

(60) Provisional application No. 60/427,808, filed on Nov. 20, 2002.

(51) Int. Cl.
*C12M 1/34* (2006.01)
*C12M 3/00* (2006.01)
*C07H 21/04* (2006.01)
*C12Q 1/68* (2006.01)

(52) U.S. Cl. .................. 435/287.2; 536/23.1; 536/24.3; 435/91.1

(58) Field of Classification Search ...................... None
See application file for complete search history.

(56) References Cited

U.S. PATENT DOCUMENTS

| | | | |
|---|---|---|---|
| 4,275,149 A | 6/1981 | Litman et al. | |
| 4,277,437 A | 7/1981 | Maggio | |
| 4,366,241 A | 12/1982 | Tom et al. | |
| 5,143,854 A | 9/1992 | Pirrung et al. | |
| 5,324,633 A | 6/1994 | Fodor et al. | |
| 5,679,523 A | 10/1997 | Li et al. | |
| 5,723,594 A | 3/1998 | Janjic et al. | |
| 5,800,992 A | 9/1998 | Fodor et al. | |
| 6,077,873 A | 6/2000 | Chanchik et al. | |
| 6,309,822 B1 * | 10/2001 | Fodor et al. | 435/6 |
| 6,344,339 B1 | 2/2002 | Menrad et al. | |
| 6,461,807 B1 | 10/2002 | Friend et al. | |
| 6,821,724 B1 | 11/2004 | Mittman et al. | |

FOREIGN PATENT DOCUMENTS

| | | |
|---|---|---|
| WO | WO 90/15070 | 12/1990 |
| WO | WO 92/10092 | 6/1992 |
| WO | WO 92/10588 | 6/1992 |

OTHER PUBLICATIONS

Marshall, Science, vol. 292, May 4, 2001; p. 822.*
Marshall, Science, vol. 296, May 10, 2002; p. 1005.*
Affymetrix Murine Genome U74 Set, version 2 (Mar. 2001).*
Affymetrix, Inc.; Product Information; GENECHIP Mu6500 Set; (1998).
Affymetrix, Inc.; Product Information; GENECHIP Mouse Expression Set 430; (2004).
Affymetrix, Inc.; Product Information; GENECHIP Murine Genome U74 Set; (2001).
Affymetrix, Inc.; Product Information; GENECHIP Murine 11K Set (2001).
Affymetrix, Inc.; Product Information; Murine 19K Set (1998).
Tanaka, et al; Genome-wide Expression Profiling of mid-gestation placenta and embryo using a 15,000 mouse developmental cDNA microarray; PNAS; Aug. 1, 2000; vol. 97; No. 16; pp. 9127-9132.
Wigle et al; Mining Mouse Microarray Data; Genome Biology; vol. 2; No. 7.
Fodor et al. "Light-directed, spatially addressable parallel chemical synthesis." Science. Feb. 15, 1991;251(4995):767-73.
Wodicka et al. "Genome-wide expression monitoring in *Saccharomyces cerevisiae*." Nat Biotechnol. Dec. 1997;15(13):1359-67.
Zhang et al. "Gene expression profiles in normal and cancer cells."Science. May 23, 1997;276(5316):1268-72.
Fox et al. "The serine/threonine kinase Pim-2 is a transcriptionally regulated apoptotic inhibitor." Genes Dev. Aug. 1, 2003;17(15):1841-54. Epub Jul. 17, 2003.
Devireddy and Green. "Transcriptional program of apoptosis induction following interleukin 2 deprivation: identification of RC3, a calcium/calmodulin binding protein, as a novel proapoptotic factor." Mol Cell Biol. Jul. 2003;23(13):4532-41.
Tietjen et al. "Single-cell transcriptional analysis of neuronal progenitors." Neuron. Apr. 24, 2003;38(2):161-75.
Mong et al. "Estradiol differentially regulates lipocalin-type prostaglandin D synthase transcript levels in the rodent brain: Evidence from high-density oligonucleotide arrays and in situ hybridization." Neuron. Apr. 24, 2003;38(2):161-75.
Oliver et al. "Transcriptional profiling of the Sonic hedgehog response: a critical role for N-myc in proliferation of neuronal precursors." Proc Natl Acad Sci U S A. Jun. 10, 2003;100(12):7331-6.
Black et al. "Distinct gene expression phenotypes of cells lacking Rb and Rb family members." Cancer Res. Jul. 1, 2003;63(13):3716-23.
Roberts and Szostak. "RNA-peptide fusions for the in vitro selection of peptides and proteins." Proc Natl Acad Sci U S A. Nov. 11, 1997;94(23):12297-302.
Cho et al. "Parallel analysis of genetic selections using whole genome oligonucleotide arrays." Proc Natl Acad Sci U S A. Mar. 31, 1998;95(7):3752-7.
Winzeler et al. "Direct allelic variation scanning of the yeast genome." Science. Aug. 21, 1998;281(5380):1194-7.
Andersson et al. "Comparative genome organization of vertebrates. The First International Workshop on Comparative Genome Organization." Mamm Genome. Oct. 1996;7(10):717-34.
Shoemaker et al. "Quantitative phenotypic analysis of yeast deletion mutants using a highly parallel molecular bar-coding strategy." Nat Genet. Dec. 1996;14(4):450-6.

* cited by examiner

*Primary Examiner*—Jehanne Sitton
(74) *Attorney, Agent, or Firm*—Sandra E. Wells

(57) ABSTRACT

The invention provides nucleic acid sequences which are complementary, in one embodiment, to a wide variety of mouse genes. The invention provides the sequences in such a way as to make them available for a variety of analyses. In one embodiment the nucleic acid sequences provided are present as an array of probes that may be used to measure gene expression of at least 30,000 mouse genes. As such, the invention relates to diverse fields impacted by the nature of molecular interaction, including chemistry, biology, medicine, and medical diagnostics.

6 Claims, No Drawings

METHODS OF GENETIC ANALYSIS OF MOUSE

RELATED APPLICATIONS

The present application claims priority to U.S. Provisional Application No. 60/427,808, filed Nov. 20, 2002, the disclosure of which is incorporated herein by reference in its entirety.

FIELD OF THE INVENTION

The present invention provides a unique pool of nucleic acid sequences useful for analyzing molecular interactions of biological interest. The invention therefore relates to diverse fields impacted by the nature of molecular interaction, including chemistry, biology, medicine, and medical diagnostics.

REFERENCE TO SEQUENCE LISTING

The Sequence Listing submitted on compact disk is hereby incorporated by reference. The file on the disk is named 3528.1seq.txt, the file is 137 MB and the date of creation is Nov. 20, 2003.

BACKGROUND OF THE INVENTION

Many biological functions are carried out by regulating the expression levels of various genes, either through changes in levels of transcription (e.g. through control of initiation, provision of RNA precursors, RNA processing, etc.) of particular genes, through changes in the copy number of the genetic DNA, through changes in RNA processing such as polyadenylation and splicing or RNA stability or through changes in protein synthesis. For example, control of the cell cycle and cell differentiation, as well as diseases, are characterized by the variations in the transcription levels of a group of genes. Gene expression is not only responsible for physiological functions, but also associated with pathogenesis. For example, the lack of sufficient functional tumor suppressor genes and/or the over expression of oncogene/protooncogenes leads to tumorgenesis. (See, e.g., Marshall, *Cell*, 64: 313-326 (1991) and Weinberg, *Science*, 254: 1138-1146 (1991)). Thus, changes in the expression levels of particular genes (e.g. oncogenes or tumor suppressors), serve as signposts for the presence and progression of various diseases. As a consequence, novel techniques and apparatus are needed to study gene expression in specific biological systems.

SUMMARY OF THE INVENTION

The invention provides nucleic acid sequences which are complementary to particular mouse genes and ESTs and makes them available for a variety of analyses, including, for example, gene expression analysis. In a preferred embodiment an array comprising nucleic acid probes where each probe is one of the sequences listed in SEQ ID Nos. 1-982,914 is disclosed. Each probe sequence may be present in a feature of known location that can be distinguished from other features that comprise probes of different sequence. For example, in one embodiment the invention comprises an array comprising any 10 or more, 100 or more, 1000 or more, 10,000 or more or 100,000 or more nucleic acid probes containing 9 or more consecutive nucleotides from the sequences listed in SEQ ID NOS: 1-982,914, or the perfect match, perfect mismatch, antisense match or antisense mismatch thereof. In a further embodiment, the invention comprises the use of any of the above arrays or fragments disclosed in SEQ ID Nos. 1-982,914 to: monitor gene expression levels by hybridization of the array to a DNA library; monitor gene expression levels by hybridization to an mRNA-protein fusion compound; identify polymorphisms; identify biallelic markers; produce genetic maps; analyze genetic variation; comparatively analyze gene expression between different species; analyze gene knockouts; or, to hybridize tag-labeled compounds. In a further embodiment the invention comprises a method of analysis comprising of hybridizing one or more pools of nucleic acids to two or more of the fragments disclosed in SEQ ID Nos. 1-982,914 and detecting said hybridization. In a further embodiment the invention comprises the use of any one or more of the fragments disclosed in SEQ ID Nos. 1-982,914 as a primer for PCR. In a further embodiment the invention comprises the use of any one or more of the fragments disclosed in SEQ ID Nos. 1-982,914 as a ligand. In another embodiment each of the sequences in SEQ ID Nos. 1-982,914 is synthesized on an array as a probe and the array is used to monitor gene expression from a biological sample isolated from mouse.

DETAILED DESCRIPTION OF THE INVENTION

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being or a mouse but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below.

However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual,* and Molecular *Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506. Genotyping arrays are described in U.S. patent application Ser. No. 10/681,773.

The present invention also contemplates sample preparation methods in certain preferred embodiments. Prior to or concurrent with hybridization to an array the nucleic acid sample may be amplified by a variety of mechanisms, some of which may employ PCR. See, e.g., *PCR Technology: Principles and Applications for DNA Amplification* (Ed. H.A. Erlich, Freeman Press, NY, N.Y., 1992); PCR Protocols: *A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and 6,582,938, each of which is incorporated herein by reference.

Additional methods of sample preparation techniques are described in Dong et al., *Genome Research* 11, 1418 (2001), in U.S. Pat. Nos. 6,361,947, 6,391,592, U.S. patent application Ser. No. 09/916,135, and U.S. Patent Publication Nos. 20030096235, 20030082543, and 20030036069.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. patent application Ser. No. 60/364,731 and in PCT Application PCT/US99/06097 (published as WO99/47964).

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. patent application Ser. No. 60/364,731 and in PCT Application PCT/US99/06097 (published as WO99/47964).

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170 and U.S. patent application Ser. No. 10/607,108.

Additionally, the present invention may have preferred embodiments that include methods for providing genetic information over networks such as the Internet as shown in U.S. patent applications Ser. Nos. 10/063,559, 60/349,546, 60/376,003, 60/394,574, 60/403,381.

I. Definitions

Massive Parallel Screening: The phrase "massively parallel screening" refers to the simultaneous screening of at least about 100, about 1000, about 10,000, about 100,000 or about 500,000 different nucleic acid hybridizations.

Nucleic Acid: The terms "nucleic acid" or "nucleic acid molecule" refer to a deoxyribonucleotide or ribonucleotide polymer in either single-or double-stranded form, and unless otherwise limited, would encompass analogs of natural nucleotides that can function in a similar manner as naturally occurring nucleotides. Nucleic acids may be derived from a variety or sources including, but not limited to, naturally occurring nucleic acids, clones, synthesis in solution or solid phase synthesis. A nucleic acid refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides, incorporation of phosphorothioate linkages, halogenated nucleosides and other nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application- .Probe: As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes. Modifications in probes may be used to improve or alter hybridization properties. Thus, probes may be peptide nucleic acids in which the constituent bases are joined by peptide bonds rather than phosphodiester linkages. Other modifications may also be used, for example, methylation or inclusion of a label or dye.

Target nucleic acid: The term "target nucleic acid" or "target sequence" refers to a nucleic acid or nucleic acid sequence which is to be analyzed. A target can be a nucleic acid to which a probe will hybridize. The probe may or may not be specifically designed to hybridize to the target. It is either the presence or absence of the target nucleic acid that is to be detected, or the amount of the target nucleic acid that is to be quantified. The term target nucleic acid may refer to the specific subsequence of a larger nucleic acid to which the probe is directed or to the overall sequence (e.g., gene or mRNA) whose expression level it is desired to detect. The difference in usage will be apparent from context.

The terms "mRNA or mRNA transcripts" as used herein, include, but are not limited to pre-mRNA transcript(s), transcript processing intermediates which may include introns, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Subsequence: "Subsequence" refers to a sequence of nucleic acids that comprise a part of a longer sequence of nucleic acids.

Perfect match: The term "match," "perfect match," "perfect match probe" or "perfect match control" refers to a nucleic acid that has a sequence that is designed to be perfectly complementary to a particular target sequence or portion thereof. For example, if the target sequence is 5'-GATTGCATA-3' the perfect complement is 5'-TATG-CAATC-3'. Where the target sequence is longer than the probe the probe is typically perfectly complementary to a portion (subsequence) of the target sequence. For example, if the target sequence is a fragment that is 800 bases, the perfect match probe may be perfectly complementary to a 25 base region of the target. A perfect match (PM) probe can be a "test probe", a "normalization control" probe, an expression level control probe and the like. A perfect match control or perfect match is, however, distinguished from a "mismatch" or "mismatch probe."

Mismatch: The term "mismatch," "mismatch control" or "mismatch probe" refers to a nucleic acid whose sequence is deliberately designed not to be perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at the center of the probe, for example if the probe is 25 bases the mismatch position is position 13, also termed the central position, such that the mismatch is most likely to destabilize the duplex with the target sequence under the test hybridization conditions. A homo-mismatch substitutes an adenine (A) for a thymine (T) and vice versa and a guanine (G) for a cytosine (C) and vice versa. For example, if the target sequence was: 5'-AGGTCCA-3', a probe designed with a single homo-mismatch at the central, or fourth position, would result in the following sequence: 3'-TCCTGGT-5', the PM probe would be 3'-TCCAGGT-5'.

Array: An "array" is a solid support with at least a first surface having a plurality of different nucleic acid sequences attached to the first surface. An array is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. Additionally, the term "array" is meant to include those libraries of nucleic acids which can be prepared by spotting nucleic acids of essentially any length (e.g., from 1 to about 1000 nucleotide monomers in length) onto a substrate.

An array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Gene Knockout: the term "gene knockout," as defined in Lodish et al. *Molecular Cell Biology* $3^{rd}$ *Edition*, Scientific American Books pub., which is hereby incorporated in its entirety for all purposes is, is a technique for selectively inactivating a gene by replacing it with a mutant allele in an otherwise normal organism.

DNA Library—as used herein the term "genomic library" or "genomic DNA library" refers to a collection of cloned DNA molecules consisting of fragments of the entire genome (genomic library) or of DNA copies of all the mRNA produced by a cell type (cDNA library) inserted into a suitable cloning vector.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which is derived from chromatin and which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

A genetic map is a map that presents the order of specific sequences on a chromosome. A genetic map expresses the positions of genes relative to each othere without a physical anchor on the chromosome. The distance between markers is typically determined by the frequency of recombination, which is related to the relative distance between markers. Genetic map distances are typically expressed as recombination units or centimorgans (cM). The physical map gives the position of a marker and its distance from other genes or markers on the same chromosome in base pairs and related to given positions along the chromosome. See, *Color Atlas of Genetics*, Ed. Passarge, Thieme, New York, N.Y. (2001), which is incorporated by reference. Genetic variation refers to variation in the sequence of the same region between two or more individuals.

Hybridization is the association of two complementary nucleic acid strands or their derivatives (such as PNA) to form double stranded molecules. Hybrids may contain, for example, two DNA strands, two RNA strands, or one DNA and one RNA strand. Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. See U.S. patent application Ser. No. 08/630,427.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al. which is hereby incorporated by reference in its entirety for all purposes above.

mRNA-protein fusion—a compound whereby an mRNA is directly attached to the peptide or protein it incodes by a stable covalent linkage.

Ligand—any molecule, other than an enzyme substrate, that binds tightly and specifically to a macromolecule, for example, a protein, forming a macromolecule-ligand complex.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementary exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. S. ee, M. Kanehisa Nucleic Acids Res. 12:203 (1984), incorporated herein by reference.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

II. Mouse Array

An array is disclosed that allows for simultaneous measurement of relative gene expression levels for at least 30,000 mouse genes. Probes of the array are designed to be complementary to 25 contiguous bases of a selected gene. Mismatch probes may be included on the array for use as controls to measure discrimination and specificity. Antisense probes that are derived from the opposite strand of the gene may also be included. Other control sequence probes may also be included. Control probes may be included to assay for manufacturing defects, problems with sample preparation and problems with hybridization. In a preferred embodiment the array is a single solid support so that the expression levels for at least 30,000 mouse genes may be simultaneously analyzed in a single experiment using a single hybridization and a single chip. See, for example the U133 Plus 2.0 Array available from Affymetrix. This array allows analysis of over 47,000 human transcripts on a single chip. In another embodiment the probes are divided so that they are on two or more solid supports. The arrays may also be attached to pegs for high throughput analysis.

SEQ ID Nos. 1-982,914, encompassed in the Sequence listing, present target sequences included in the invention. Each target sequence corresponds to and represents at least four nucleic acid sequences included in the invention. For example, if the nucleic acid to be hybridized to the array has the sequence 5'-gatgctacc-3' the additional sequences included in the invention which are represented by this nucleic acid sequence are, for example:

5'-ggtagcatc-3'=(perfect) sense match
5'-ggtaccatc-3'=sense mismatch
5'-gatgctacc-3'=(perfect) antisense match
5'-gatggtacc-3'=antisense mismatch Accordingly, for each nucleic acid sequence listed in SEQ ID Nos. 1-982,914, this disclosure includes the corresponding sense match, sense mismatch, antisense match and antisense mismatch. The position of the mismatch is not limited to the above example, it may be located anywhere in the nucleic acid sequence and may comprise one or more bases. In a preferred embodiment the mismatch is located at the central position of the probe, for example, position 13 of a 25 mer probe.

When measuring expression one of skill in the art will recognize that the probes of the array should be designed to be complementary to the sequence to be detected. This may vary depending on which amplification method is used. For example, one method of amplification calls for reverse transcription of the mRNA using an oligo-dt-T7 primer. Double stranded cDNA with an RNA polymerase promoter is then generated and antisense RNA is transcribed and labeled. The antisense RNA is then hybridized to the array. The antisense RNA is complementary to the mRNA so the sense probe on the array that is designed to hybridize to the antisense RNA is identical in sequence to a portion of the starting mRNA. In another method the amplified RNA to be hybridized to the array is sense, meaning that it has the same sequence as the starting mRNA. In other embodiments the amplification product that is hybridized to the array may be cDNA that may be of the sense (same as) or antisense (complement of) orientation relative to the starting mRNA.

Consequently, the present invention includes: a) the target sequences listed in SEQ ID Nos. 1-982,914, or the sense-match, sense mismatch, antisense match or antisense mismatch thereof; b) clones which comprise the target nucleic acid sequences listed in SEQ ID Nos. 1-982,914, or the sense-match, sense mismatch, antisense match or antisense mismatch thereof; c) longer nucleotide sequences which include the nucleic acid sequences listed in SEQ ID Nos. 1-982,914, or the sense-match, sense mismatch, antisense match or antisense mismatch thereof and d) subsequences greater than 9 nucleotides in length of the target nucleic acid sequences listed in SEQ ID Nos. 1-982,914, or the sense match, sense mismatch, antisense match or antisense mismatch.

Target sequences were chosen to include more than 36,000 full-length mouse genes and EST clusters. These sequences were chosen as predicted coding sequences from genomic BAC entries. The EST clusters share homology with the predicted coding sequences from BAC cones. Target sequences were selected using the computer based methods described in U.S. Pat. No. 6,309,822 incorporated herein by reference for all purposes.

Each target sequence listed in SEQ ID NOS 1-982,914 corresponds to a GenBank database accession number. These accession numbers allow for the identification of sequences located in the GenBank sequence database through the use of computer programs such as BLAST. Access to BLAST is available to the public through the internet. One of skill in the art will be familiar with the use of the BLAST program to obtain information about particular sequences in order to, for example, determine the Gen-Bank accession number for a given sequence, determine the species from which the sequence is derived, determine the gene from which the sequence is derived, to determine other genes and species which contain similar sequences and to determine the degree of similarity between one sequence and another. All information relating to the target sequences available through the GenBank database is hereby incorporated by reference for all purposes.

The present invention provides a pool of unique nucleotide sequences complementary to Mouse sequences in particular embodiments which alone, or in combinations of 2 or more, 10 or more, 100 or more, 1,000 or more, 10,000 or more, or 100,000 or more, can be used for a variety of applications.

In one embodiment, the present invention provides for a pool of unique nucleotide sequences which are complementary to approximately 36,000 Mouse genes and ESTs formed into a high density array of probes suitable for array based massive parallel gene expression. Array based methods for monitoring gene expression are disclosed and discussed in detail in U.S. Pat. No. 5,800,992, U.S. Pat. No. 6,309,822, and PCT Application WO 92/10588 (published on Jun. 25, 1992), all of which are incorporated herein by reference for all purposes. Generally those methods of monitoring gene expression involve (1) providing a pool of target nucleic acids comprising RNA transcript(s) of one or more target gene(s), or nucleic acids derived from the RNA transcript(s);

(2) hybridizing the nucleic acid sample to a high density array of probes and (3) detecting the hybridized nucleic acids and calculating a relative expression (transcription, RNA processing or degradation) level.

The development of Very Large Scale Immobilized Polymer Synthesis or VLSIPS™ technology has provided methods for making very large arrays of nucleic acid probes in very small arrays. See U.S. Pat. No. 5,143,854 and PCT Patent Publication Nos. WO 90/15070 and WO 92/10092, and Fodor et al., *Science*, 251, 767-77 (1991), each of which is incorporated herein by reference. U.S. Pat. No. 5,800,992, describes methods for making arrays of nucleic acid probes that can be used to detect the presence of a nucleic acid containing a specific nucleotide sequence. Methods of forming high density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling.

In a preferred detection method, the array of immobilized nucleic acids, or probes, is contacted with a sample containing target nucleic acids, to which a flourescent label is attached. Target nucleic acids hybridize to the probes on the array and any non-hybridized nucleic acids are removed. The array containing the hybridized target nucleic acids are exposed to light which excites the flourescent label. The resulting flourescent intensity, or brightness, is detected. Relative brightness is used to determine which probe is the best candidate for the perfect match to the hybridized target nucleic acid because flourescent intensity (brightness) corresponds to binding affinity. Once the position of the perfect match probe is known, the sequence of the hybridized target nucleic is known because the sequence and position of the probe is known.

In the array of the present invention the probes are presented in pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether a hybridization is or is not specific. For example, if the target is present, the perfect match probes should be consistently brighter than the mismatch probes because fluorescence intensity, or brightness, corresponds to binding affinity. (See, for example U.S. Pat. No. 5,324,633, which is incorporated herein for all purposes.) In addition, if all central mismatches are present, the mismatch probes can be used to detect a mutation. Finally the difference in intensity between the perfect match and the mismatch probe (I(PM)-I(MM)) provides a good measure of the concentration of the hybridized material. See pending PCT Application No. 98/11223, which is incorporated herein by reference for all purposes. The probe pairs are presented in both sense and antisense orientation, thereby eliciting a total of four probes per target sequence: sense match, sense mismatch, antisense match and antisense mismatch.

In another embodiment, the current invention provides a pool of sequences which may be used as probes for their complementary genes listed in the genbank database. Methods for making probes are well known. See for example Sambrook, Fritsche and Maniatis. "Molecular Cloning A laboratory Manual" 2$^{nd}$ Ed. Cold Spring Harbor Press (1989) ("Maniatis et al.") which is hereby incorporated in its entirety by reference for all purposes. Maniatis et al. describes a number of uses for nucleic acid probes of defined sequence. Some of the uses described by Maniatis et al. include: to screen cDNA or genomic DNA libraries, or subclones derived from them, for additional clones containing segments of DNA that have been isolated and previously sequenced; in Southern, northern, or dot-blot hybridization to identify or detect the sequences of specific genes; in Southern, or dot-blot hybridization of genomic DNA to detect specific mutations in genes of known sequence; to detect specific mutations generated by site-directed mutagenesis of cloned genes; and to map the 5' termini of mRNA molecules by primer extensions. Maniatis et al. describes other uses for probes throughout. See also Alberts et al. *Molecular Biology of the Cell* 3$^{rd}$ *edition*, Garland Publishing Inc. (1994) p. 307 and Lodish et al. *Molecular Cell Biology*, 3$^{rd}$ *edition*, Scientific American Books (1995) p. 285-286, each of which is hereby incorporated by reference in its entirety for all purposes, for a brief discussion of the use of nucleic acid probes in in situ hybridization. Other uses for probes derived from the sequences disclosed in this invention will be readily apparent to those of skill in the art. See, for example, Lodish et al. *Molecular Cell Biology*, 3$^{rd}$ *edition*, Scientific American Books (1995) p. 229-233, incorporated above, for a description of the construction of genomic libraries.

In another embodiment, the current invention may be combined with known methods to monitor expression levels of genes in a wide variety of contexts. For example, where the effects of a drug on gene expression are to be determined, the drug will be administered to an organism, a tissue sample, or a cell and the gene expression levels will be analyzed. For example, nucleic acids are isolated from the treated tissue sample, cell, or a biological sample from the organism and from an untreated organism tissue sample or cell, hybridized to a high density probe array containing probes directed to the gene of interest and the expression levels of that gene are determined. The types of drugs that may be used in these types of experiments include, but are not limited to, antibiotics, antivirals, narcotics, anti-cancer drugs, tumor suppressing drugs, and any chemical composition which may affect the expression of genes in vivo or in vitro. The current invention is particularly suited to be used in the types of analyses described by, for example, U.S. Pat. No. 6,309,822 and PCT Application No. 98/11223, each of which is incorporated by reference in its entirety for all purposes. As described in Wodicka et al., Nature Biotechnology 15 (1997), hereby incorporated by reference in its entirety for all purposes, because mRNA hybridization correlates to gene expression level, hybridization patterns can be compared to determine differential gene expression. As non-limiting examples: hybridization patterns from samples treated with certain types of drugs may be compared to hybridization patterns from samples which have not been treated or which have been treated with a different drug; hybridization patterns for samples infected with a specific virus may be compared against hybridization patterns from non-infected samples; hybridization patterns for samples with cancer may be compared against hybridization patterns for samples without cancer; hybridization patterns of samples from cancerous cells which have been treated with a tumor suppressing drug may be compared against untreated cancerous cells, etc. Zhang et al., Science 276 1268-1272, hereby incorporated by reference in its entirety for all purposes, provides an example of how gene expression data can provide a great deal of insight into cancer research. One skilled in the art will appreciate that a wide range of applications will be available using 2 or more, 10 or more, 100 or more, 1000 or more, 10,000 or more or 100,000 or more of the SEQ ID Nos. 1-982,914 sequences as probes for gene expression analysis. The combination of the nucleic acid array technology and the Mouse specific probes in this disclosure is a powerful tool for studying gene expression. Mouse arrays have been used by researchers in a variety of studies. See, for example, Fox, C. J. et al. Genes & Development 17, 1841-54, 2003, Black, E. P. et al. Cancer Research 63, 3716-23, 2003, Devireddy, L. R. et al. Molecular and Cellular Biology 23, 4532-41, 2003, Tietjen, I. et al. Neuron 38(2), 161-75, 2003, Mong, J. A. et al. Proceedings of the National Academy of Sciences of the United States of America 100(1), 318-23, 2003, and Oliver, T. G. et al. Proceedings of the National Academy of Sciences of the United States of America 100(12), 7331-6, 2003.

In another embodiment, the invention may be used in conjunction with the techniques which link specific proteins to the mRNA which encodes the protein. (See for example Roberts and Szostak Proc. Natl, Acad. Sci. 94 12297-12302 (1997), which is incorporated herein in its entirety for all purposes.) Hybridization of these mRNA-protein fusion compounds to arrays comprised of 2 or more, 10 or more, 100 or more, 1000 or more, 10,000 or more, or 100,000 or more the sequences disclosed in the present invention provides a powerful tool for monitoring expression levels.

In one embodiment, the current invention provides a pool of unique nucleic acid sequences which can be used for parallel analysis of gene expression under selective conditions. Without wishing to be limited, genetic selection under selective conditions could include: variation in the temperature of the organism's environment; variation in pH levels in the organism's environment; variation in an organism's food (type, texture, amount etc.); variation in an organism's surroundings; etc. Arrays, such as those in the present invention, can be used to determine whether gene expression is altered when an organism is exposed to selective conditions.

Methods for using nucleic acid arrays to analyze genetic selections under selective conditions are known. (See for example, R. Cho et al., Proc. Natl. Acad. Sci. 95 3752-3757 (1998), incorporated herein in its entirety for all purposes.) Cho et al. describes the use of a high-density array containing oligonucleotides complementary to every gene in the yeast *Saccharomyces cerevisiae* to perform two-hybrid protein-protein interaction screens for *S. cerevisiae* genes implicated in mRNA splicing and microtubule assembly. Cho et al. was able to characterize the results of a screen in a single experiment by hybridization of labeled DNA derived from positive clones. Briefly, as described by Cho et al., two proteins are expressed in yeast as fusions to either the DNA-binding domain or the activation domain of a transcription factor. Physical interaction of the two proteins reconstitutes transcriptional activity, turning on a gene essential for survival under selective conditions. In screening for novel protein-protein interactions, yeast cells are first transformed with a plasmid encoding a specific DNA-binding fusion protein. A plasmid library of activation domain fusions derived from genomic DNA is then introduced into these cells. Transcriptional activation fusions found in cells that survive selective conditions are considered to encode peptide domains that may interact with the DNA-binding domain fusion protein. Clones are then isolated from the two-hybrid screen and mixed into a single pool. Plasmid DNA is purified from the pooled clones and the gene inserts are amplified using PCR. The DNA products are then hybridized to yeast whole genome arrays for characterization. The methods employed by Cho et al. are applicable to the analysis of a range of genetic selections. High density arrays created using two or more, 10 or more, 100 or more, 1000 or more, 10,000 or more, or 100,000 or more of the sequences disclosed in the current invention can be used to analyze genetic selections in the mouse system using the methods described in Cho et al.

In another embodiment, the current invention provides a pool of unique nucleic acid sequences which can be used to identify biallelic markers, providing a novel and efficient approach to the study of genetic variation. For example, methods for using high density arrays comprised of probes which are complementary to the genomic DNA of a particular species to interrogate polymorphisms are well known. (See for example, U.S. Pat. No. 6,300,063 which is hereby incorporated by reference herein for all purposes.) Pools of 2 or more, 10 or more, 100 or more, 1000 or more, 10,000 or more, or 100,000 or more of the sequences disclosed in this invention combined with the methods described in the above patent provides a tool for studying genetic variation in the Mouse system.

In another embodiment of the invention, genetic variation can be used to produce genetic maps of various strains of Mouse. Winzeler et al., "Direct Allelic Variation Scanning of the Yeast Genome" Science. 281(5380):1194-7. (1998), which is hereby incorporated for all purposes describes methods for conducting this type of screening with arrays containing probes complementary to the yeast genome. Briefly, genomic DNA from strains which are phenotypically different are isolated, fragmented, and labeled. Each strain is then hybridized to identical arrays comprised of the nucleic acid sequences complementary to the system being studied. Comparison of hybridization patterns between the various strains then serve as genetic markers. As described by Winzler et al, these markers can then be used for linkage analysis. High density arrays created from 2 or more, 10 or more, 100 or more, 1000 or more, 10,000 or more, or 100,000 or more of the sequences disclosed in this invention can be used to study genetic variation using the methods described by Winzler et al.

In another embodiment genetic variation may be correlated with variation in gene expression pattern. Much of the genetic variation between individuals is the result of single nucleotide polymorphisms (SNPs). The presence of SNPs in or near a gene may result in differences in gene expression, which may result, for example, from changes in the rate of transcription, the stability of the mRNA, splicing of the mRNA, or translation of the mRNA. In one embodiment an array comprising SEQ ID Nos. 1-982,914 and probes to genotype selected SNPs in the mouse genome may be used to monitor genotype and expression changes that correlate with differences in genotype.

In another embodiment, the present invention may be used for cross-species comparisons. One skilled in the art will appreciate that it is often useful to determine whether a gene present in one species, for example mouse, is present in a conserved format in another species, including, without limitation, *Drosophila*, human, chicken, zebrafish, *Escherichia coli*, or yeast. See, for example, Andersson et al., Mamm. Genome 7(10):717-734 (1996), which is hereby incorporated by reference for all purposes, which describes the utility of cross-species comparisons. The use of 2 or more, 10 or more, 100 or more, 1000 or more, 10,000 or more or 100,000 or more of the sequences disclosed in this invention in an array can be used to determine whether any of the sequence from one or more of the mouse genes represented by the sequences disclosed in this invention is conserved in another species by, for example, hybridizing genomic nucleic acid samples from another species to an array comprised of the sequences disclosed in this invention. Areas of hybridization will yield genomic regions where the nucleotide sequence is highly conserved between the interrogation species and the mouse.

In another embodiment, the present invention may be used to characterize the genotype of knockouts. Methods for using gene knockouts to identify a gene are well known. See for example, Lodish et al. *Molecular Cell Biology*, 3rd Edition, Scientific American Books pub pp. 292-296 and U.S. Pat. No. 5,679,523, which are hereby incorporated by reference for all purposes. By isolating genomic nucleic acid samples from knockout species with a known phenotype and hybridizing the samples to an array comprised of 2 or more, 10 or more, 100 or more, 1000 or more, 10,000 or more, or 100,000 or more of the sequences disclosed in this invention, candidates genes which contribute to the phenotype will be identified and made accessible for further characterization.

In another embodiment, the present invention may be used to identify new gene family members. Methods of screening libraries with probes are well known. (See, for example, Maniatis et al, incorporated by reference above.) Because the present invention is comprised of nucleic acid sequences from specific known genes, 2 or more, 10 or more, 100 or more, 1000 or more, 10,000 or more, or 100,000 or more of sequences disclosed in this invention may be used as probes to screen genomic libraries to look for additional family members of those genes from which the target sequences are derived.

In another embodiment, the present invention may be used to provide nucleic acid sequences to be used as tag sequences. Tag sequences are a type of genetic "bar code" which can be used to label compounds of interest. The analysis of deletion mutants using tag sequences is described in, for example, Shoemaker et al., Nature Genetics 14 450-456 (1996), which is hereby incorporated by reference in its entirety for all purposes. Shoemaker et al. describes the use of PCR to generate large numbers of deletion strains. Each deletion strain is labeled with a unique 20-base tag sequence that can be hybridized to a high-density oligonucleotide array. The tags serve as unique identifiers (molecular bar codes) that allow analysis of large numbers of deletion strains simultaneously through selective growth conditions. The use of tag sequences need not be limited to this example however. The utility of using unique known short oligonucleotide sequences capable of hybridizing to a nucleic acid array to label various compounds will be apparent to one skilled in the art. One or more, 10 or more, 100 or more, 1000 or more, 10,000 or more, or 100,000 or more of the SEQ ID Nos. 1-982,914 sequences are excellent candidates to be used as tag sequences.

In another embodiment of the invention, the sequences of this invention may be used to generate primers directed to their corresponding genes as disclosed in the Genbank or any other public database. These primers may be used in such basic techniques as sequencing or PCR, see for example Maniatis et al., incorporated by reference above.

In another embodiment, the invention provides a pool of nucleic acid sequences to be used as ligands for specific genes. The sequences disclosed in this invention may be used as ligands to their corresponding genes as disclosed in the Genbank or any other public database. Compounds which specifically bind known genes are of interest for a variety of uses. One particular clinical use is to act as an antisense protein which specifically binds and disables a gene which has been, for example, linked to a disease. Methods and uses for ligands to specific genes are known. See for example, U.S. Pat. No. 5,723,594, which is hereby incorporated by reference in its entirety for all purposes.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), phosphorescent labels, enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993), which is hereby incorporated by reference in its entirety for all purposes.

Fluorescent labels are preferred and easily added during an in vitro transcription reaction. In a preferred embodiment, fluorescein labeled UTP and CTP are incorporated into the RNA produced in an in vitro transcription reaction as described above.

EXAMPLE

The following example serves to illustrate the type of experiment that could be conducted using the invention.

Expression Monitoring by Hybridization to High Density Oligonucleotide Arrays

Arrays containing the desired number of probes can be synthesized using the method described in U.S. Pat. No. 5,143,854, incorporated by reference above. Extracted poly $(A)^+$ RNA can then be coverted to cDNA using the methods described below. The cDNA is then transcribed in the presence of labeled ribonucleotide triphosphates. The label may be biotin or a dye such as fluorescein. RNA is then fragmented with heat in the presence of magnesium ions. Hybridizations are carried out in a flow cell that contains the two-dimensional DNA probe arrays. Following a brief washing step to remove unhybridized RNA, the arrays are scanned using a scanning confocal microscope.

1. A Method of RNA Preparation:

Labeled RNA is prepared from clones containing a T7 RNA polymerase promoter site by incorporating labeled ribonucleotides in an IVT reaction. Either biotin-labeled or fluorescein-labeled UTP and CTP (1:3 labeled to unlabeled) plus unlabeled ATP and GTP is used for the reaction with 2500 U of T7 RNA polymerase. Following the reaction unincorporated nucleotide triphosphates are removed using size-selective membrane such as Microcon—100, (Amicon, Beverly, Mass.). The total molar concentration of RNA is based on a measurement of the absorbance at 260 nm. Following quantitation of RNA amounts, RNA is fragmented randomly to an average length of approximately 50 bases by heating at 94° in 40 mM Tris-acetate pH 8.1, 100 mM potassium acetate, 30 mM magnesium acetate, for 30 to 40 min. Fragmentation reduces possible interference from RNA secondary structure, and minimizes the effects of multiple interactions with closely spaced probe molecules. For material made directly from cellular RNA, cytoplasmic RNA is extracted from cells by the method of Favaloro et al. Methods Enzymol. 65:718-749 (1980) hereby incorporated by reference for all purposes, and poly $(A)^+$ RNA is isolated with an oligo dT selection step using, for example, Poly Atract, (Promega, Madison, Wis.). RNA can be amplified using a modification of the procedure described by Eberwine et al. Proc. Natl. Acad. Sci. USA 89:3010-3014 (1992), hereby incorporated by reference for all purposes. Microgram amounts of poly $(A)^+$ RNA are converted into double stranded cDNA using a cDNA synthesis kit (kits may be obtained from Life Technologies, Gaithersburg, Md.) with an oligo dT primer incorporating a T7 RNA polymerase promoter site. After second-strand synthesis, the reaction mixture is extracted with phenol/chloroform, and the double-stranded DNA isolated using a membrane filtration step using, for example, Microcon—100, (Amicon).

Labeled cRNA can be made directly from the cDNA pool with an IVT step as described above. The total molar concentration of labeled cRNA is determined from the absorbance at 260 nm and assuming an average RNA size of 1000 ribonucleotides. The commonly used convention is that 1 OD is equivalent to 40 ug of RNA, and that 1 ug of cellular mRNA consists of 3 pmol of RNA molecules. Cellular mRNA may also be labeled directly without any intermediate cDNA synthesis steps. In this case, Poly $(A)^+$ RNA is fragmented as described, and the 5' ends of the fragments are kinased and then incubated overnight with a biotinylated oligoribonucleotide (5'-biotin-AAAAAA-3') in the presence of T4 RNA ligase (available from Epicentre Technologies, Madison, Wis.). Alternatively, mRNA has been labeled directly by UV-induced cross-linking to a psoralen derivative linked to biotin (available from Schleicher & Schuell, Keene, N.H.).

2. Array Hybridization and Scanning:

Array hybridization solutions can be made containing 0.9 M NaCl, 60 mM EDTA, and 0.005% Triton X-100, adjusted to pH 7.6 (referred to as 6×SSPE-T). In addition, the solutions should contain 0.5 mg/ml unlabeled, degraded herring sperm DNA (available from Sigma, St. Louis, Mo.). Prior to hybridization, RNA samples are heated in the hybridization solution to 99° C. for 10 min, placed on ice for 5 min, and allowed to equilibrate at room temperature before being placed in the hybridization flow cell. Following hybridization, the solutions are removed, the arrays washed with 6×SSPE-T at 22° C. for 7 min, and then washed with 0.5×SSPE-T at 40° C. for 15 min. When biotin labeled RNA is used the hybridized RNA should be stained with a streptavidin-phycoerythrin in 6×SSPE-T at 40° C. for 5 min. The arrays are read using a scanning confocal microscope made by Molecular Dynamics (commercially available through Affymetrix, Santa Clara, Calif.). The scanner uses an argon ion laser as the excitation source, with the emission detected by a photomultiplier tube through either a 530 nm bandpass filter (flourescein) or a 560 nm longpass filter (phycoerythrin). Nucleic acids of either sense or antisense orientations may be used in hybridization experiments. Arrays for probes with either orientation (reverse complements of each other) are made using the same set of photolithgraphic masks by reversing the order of the photochemical steps and incorporating the complementary nucleotide.

3. Quantitative Analysis of Hybridization Patterns and Intensities:

Following a quantitative scan of an array, a grid is aligned to the image using the known dimensions of the array and the corner control regions as markers. The image is then reduced to a simple text file containing position and intensity information using software developed at Affymetrix (available with the confocal scanner). This information is merged with another text file that contains information relating physical position on the array to probe sequence and the identity of the RNA (and the specific part of the RNA) for which the oligonucleotide probe is designed. The quantitative analysis of the hybridization results involves a simple form of pattern recognition based on the assumption that, in the presence of a specific RNA, the perfect match (PM) probes will hybridize more strongly on average than their mismatch (MM) partners. The number of instances in which the PM hybridization is larger than the MM signal is computed along with the average of the logarithm of the PM/MM ratios for each probe set. These values are used to make a decision (using a predefined decision matrix) concerning the presence or absence of an RNA. To determine the quantitative RNA abundance, the average of the difference (PM-MM) for each probe family is calculated. The advantage of the difference method is that signals from random cross-hybridization contribute equally, on average, to the PM and MM probes, while specific hybridization contributes more to the PM probes. By averaging the pairwise differences, the real signals add constructively while the contributions from cross-hybridization tend to cancel. When assessing the differences between two different RNA samples, the hybridization signals from side-by-side experiments on identically synthesized arrays are compared directly. The magnitude of the changes in the average of the difference (PM-MM) values is interpreted by comparison with the results of spiking experiments as well as the signals observed for the internal standard bacterial and phase RNAs spiked into each sample at a known amount. Data analysis programs, such as those described in U.S. Pat. No. 6,600,996 perform these operations automatically. For additional methods of expression analysis see the GeneChip® Expression Analysis Technical Manual (2002), available from Affymetrix, Inc. which is hereby incorporated by reference for all purposes.

CONCLUSION

The inventions herein provide a pool of unique nucleic acid sequences which are complementary to approximately 36,000 full-length mouse genes and EST clusters from Unigene database (build 107). These sequences can be used for a variety of types of analyses.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07250289B2). An electronic copy of the "Sequence Listing" will also be available from the USPTO upon request and payment of the fee set forth in 37 CFR 1.19(b)(3).

What is claimed is:

1. An array comprising a plurality of nucleic acid probes, wherein the plurality comprises each of the sequences listed in SEQ ID NOS 1-982,914, and wherein each probe in the plurality of nucleic acid probes consists of one of the sequence listed in SEQ ID NOS: 1-982,914.

2. The array of claim 1 further comprising at least one probe that is the perfect complement of one of the sequences listed in SEQ ID Nos. 1-982,914.

3. The array of claim 1 further comprising at least one probe that is the mismatch probe corresponding to one of the sequences listed in SEQ ID Nos. 1-982,914, wherein the mismatch position is the central position.

4. The array of claim 1 wherein said plurality of nucleic acid probes is attached to a solid support.

5. The array of claim 1 wherein the array comprises a plurality of beads wherein the probes are attached to the beads and the probes on a bead consist of one of the sequences listed in SEQ ID Nos. 1-982,914.

6. The array of claim 1 wherein the array consists of a single contiguous solid support.

* * * * *